(12) United States Patent
Matsumoto et al.

(10) Patent No.: US 8,307,698 B2
(45) Date of Patent: Nov. 13, 2012

(54) VIBRATING WIRE VISCOMETERS

(75) Inventors: Noriyuki Matsumoto, Yokohama (JP); Sophie Nazik Godefroy, Cairo (EG); Kazumasa Kato, Yokohama (JP); Go Fujisawa, Sagamihara (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 573 days.

(21) Appl. No.: 12/537,257

(22) Filed: Aug. 7, 2009

(65) Prior Publication Data
US 2011/0030455 A1 Feb. 10, 2011

(51) Int. Cl.
G01N 11/10 (2006.01)
(52) U.S. Cl. ............. 73/54.41; 73/54.02; 73/54.24; 73/54.25; 73/54.26; 73/54.27
(58) Field of Classification Search .......... 73/54.23–29, 73/53.31–32, 64.53, 54.02, 54.41
See application file for complete search history.

(56) References Cited

U.S. PATENT DOCUMENTS

| | | | |
|---|---|---|---|
| 4,860,581 A | 8/1989 | Zimmerman et al. | |
| 4,936,139 A | 6/1990 | Zimmerman et al. | |
| 6,584,833 B1 * | 7/2003 | Jamison et al. | 73/61.63 |
| 7,194,902 B1 * | 3/2007 | Goodwin et al. | 73/152.24 |
| 7,222,671 B2 * | 5/2007 | Caudwell et al. | 166/252.5 |
| 7,412,877 B1 | 8/2008 | Bi | |
| 7,520,162 B2 * | 4/2009 | Wenger et al. | 73/54.41 |
| 7,574,898 B2 * | 8/2009 | Harrison et al. | 73/54.41 |
| 7,634,939 B2 * | 12/2009 | Drahm et al. | 73/54.25 |
| 2001/0039829 A1 * | 11/2001 | Wenger et al. | 73/54.41 |
| 2006/0137873 A1 | 6/2006 | Caudwell et al. | |
| 2010/0263862 A1 * | 10/2010 | Goodwin | 166/252.5 |
| 2011/0023587 A1 * | 2/2011 | Madhavan et al. | 73/54.41 |

FOREIGN PATENT DOCUMENTS

| | | |
|---|---|---|
| GB | 2421573 | 6/2006 |
| GB | 2456034 | 7/2009 |
| WO | 2008/113026 | 9/2008 |
| WO | 2009/061563 | 5/2009 |

* cited by examiner

*Primary Examiner* — Hezron E Williams
*Assistant Examiner* — Hoang Nguyen
(74) *Attorney, Agent, or Firm* — Jianguang Du; Jody DeStefanis

(57) ABSTRACT

Vibrating wire viscometers are disclosed. An example vibrating wire viscometer includes first and second electrically conductive tubes, where the first tube is at least partially inserted into the second tube, and where the first and second tubes are coupled via an electrically insulating bonding agent. The example viscometer further includes first and second electrically conductive pins inserted into respective ones of the first and second tubes, and an electrically conductive wire fastened to the first and second pins to vibrate in a downhole fluid to determine a viscosity of the downhole fluid.

20 Claims, 5 Drawing Sheets

VIBRATING WIRE VISCOMETERS

FIELD OF THE DISCLOSURE

This disclosure relates generally to viscosity testing of downhole fluids and, more particularly, to vibrating wire viscometers.

BACKGROUND

In the field of downhole petroleum and natural gas exploration, fluid property measurement is an important tool to surveyors to understand the economic viability of a subterranean formation. Among the fluid properties of interest is viscosity. However, the downhole environments in which such fluid properties are determined may cause problems for the tools used to collect data. For example, the heat, pressure, shock, and vibration present in the downhole environment may cause deterioration of the tools and/or loss of measurement accuracy.

SUMMARY

Vibrating wire viscometers are described herein. Some example vibrating wire viscometers described herein include first and second electrically conductive tubes, where the first tube is at least partially inserted into the second tube, and where the first and second conductive tubes are coupled via an electrically insulating bonding agent. The example viscometers may further include first and second electrically conductive pins inserted into respective ones of the first and second tubes, and an electrically conductive wire fastened to the first and second pins to vibrate in a downhole fluid to determine a viscosity of the downhole fluid.

Other vibrating wire viscometers described herein include first and second electrically conductive tubes disposed in a housing, where the first tube is at least partially inserted into the second tube, and wherein the first and second tubes are coupled via an electrically insulating bonding agent. The example vibrating wire viscometers may further include first and second electrically conductive pins inserted in parallel into respective ones of the first and second tubes, an electrically conductive wire held in tension between the first and second pins to vibrate in a downhole fluid in the first and second tubes, a magnet to generate a magnetic field adjacent the wire, a signal processor to generate an electrical signal to cause the wire to vibrate at a resonance frequency in the magnetic field, and an analyzer to measure a reverse voltage of the wire to determine a viscosity of the downhole fluid.

Some other example vibrating wire viscometers described herein include first and second electrically conductive tubes, where the first tube is at least partially inserted into the second tube, and where the first and second tubes are coupled via an electrically insulating bonding agent. The example vibrating wire viscometer may further include first and second electrically conductive pins inserted in parallel into respective ones of the first and second tubes, an electrically conductive wire held in tension between the first and second pins to vibrate in a downhole fluid in the first and second tubes, and a housing. The example housing includes a flowline, where the first and second tubes are disposed in the flowline, a magnet disposed in the housing to generate a magnetic field around the wire, a signal processor to generate an electrical signal to vibrate the wire in the magnetic field at a resonance frequency, and an analyzer to measure a reverse voltage on the wire to determine a viscosity of the downhole fluid.

DETAILED DESCRIPTION

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness. Accordingly, while the following describes example systems, persons of ordinary skill in the art will readily appreciate that the examples are not the only way to implement such systems.

The example vibrating wire viscometers described herein may be used in downhole fluid sampling operations. Some example vibrating wire viscometer configurations described herein include two electrically conductive tubes coupled via a non-conductive (e.g., electrically insulating) bonding agent. In some examples, electrically conductive pins are then inserted (e.g., press fitted) into each tube. An electrically conductive wire is held in tension between the pins by crimping the pins around the wire. In some examples, the tubes and/or pins may be oriented to prevent twisting of the wire. Additionally, the tubes, the pins, the wire, and/or the non-conductive bonding agent may have similar thermal expansion coefficients. Thus, when the example vibrating wire viscometers described herein are exposed to varying downhole temperatures, the tension of the wire remains substantially constant and the measurement accuracy of the viscometers is maintained.

In some examples, the example tensioned wire is exposed to (e.g., immersed in) a downhole fluid. Magnets on either side of the wire generate a magnetic field across the wire, and an alternating current is passed through the wire via the conductive tubes and/or via electrodes. As a result, the wire may vibrate at a resonance frequency, the damping of which may be used by an analyzer to determine the viscosity of the downhole fluid to which the wire is exposed.

Figure 1:
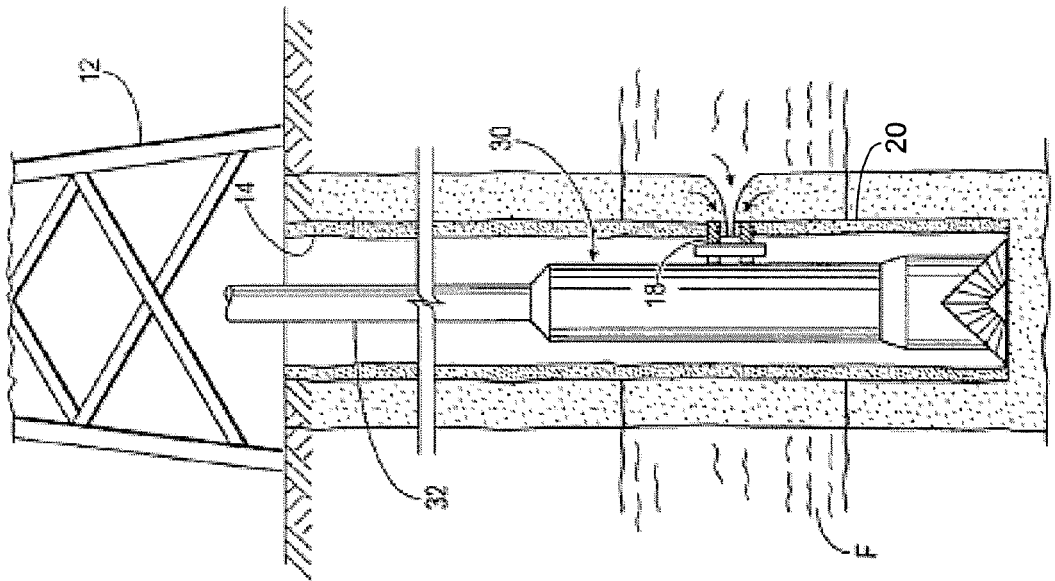
FIG. 1 depicts a wireline tool that is suspended from a rig into a wellbore and which may employ the example vibrating wire viscometers described herein.

FIG. 1 depicts a wireline tool 10 that is suspended from a rig 12 into a wellbore 14 and which may employ the example vibrating wire viscometers described herein. The downhole tool 10 can be any type of tool capable of performing formation evaluation. The downhole tool 10 of FIG. 1 is deployed from the rig 12 into the wellbore 14 via a wireline cable 16 and positioned adjacent to a formation F. The downhole tool 10 is provided with a probe 18 adapted to seal against a wall 20 of the wellbore 14 (hereinafter referred to as a "wall 20" or "wellbore wall 20") and draw fluid from the formation F into the downhole tool 10 as depicted by the arrows. Backup pistons 22 and 24 assist in pushing the probe 18 of the downhole tool 10 against the wellbore wall 20.

Figure 2:
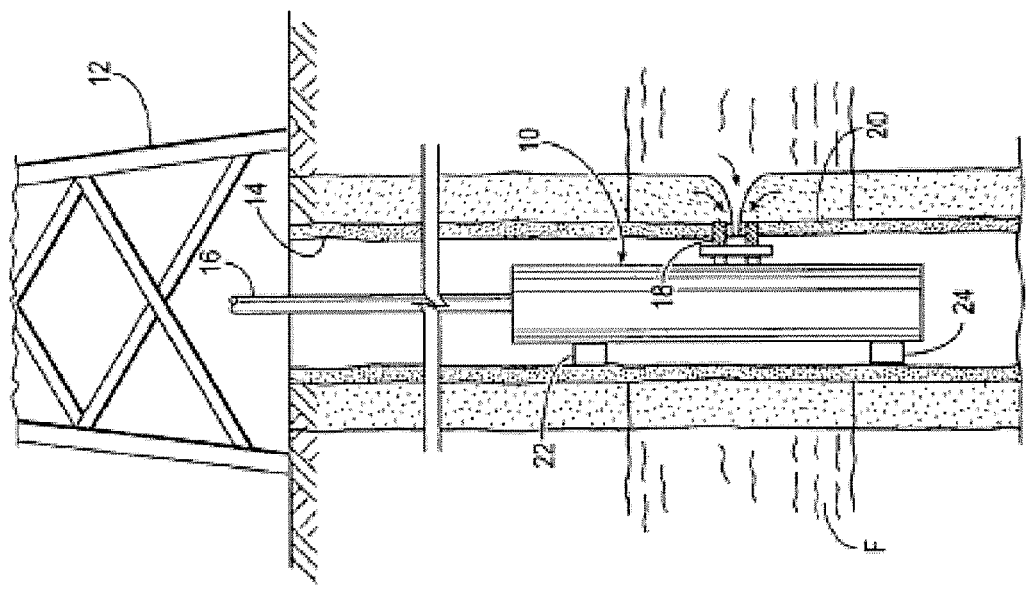
FIG. 2 depicts a drillstring tool that may employ the example vibrating wire viscometers described herein.

FIG. 2 depicts a drillstring tool 30 that may employ the example vibrating wire viscometers described herein. The downhole tool 30 of FIG. 2 is a drilling tool, which can be conveyed among one or more (or itself may be) a measurement-while-drilling (MWD) drilling tool, a logging-while-drilling (LWD) drilling tool, or other type of drilling tool known to those skilled in the art. The downhole tool 30 is attached to a drill string 32 driven by the rig 12 to form the wellbore 14. The downhole tool 30 includes the probe 18 adapted to seal against the wall 20 of the wellbore 14 to draw fluid from the formation F into the downhole tool 30 as depicted by the arrows.

Figure 3:
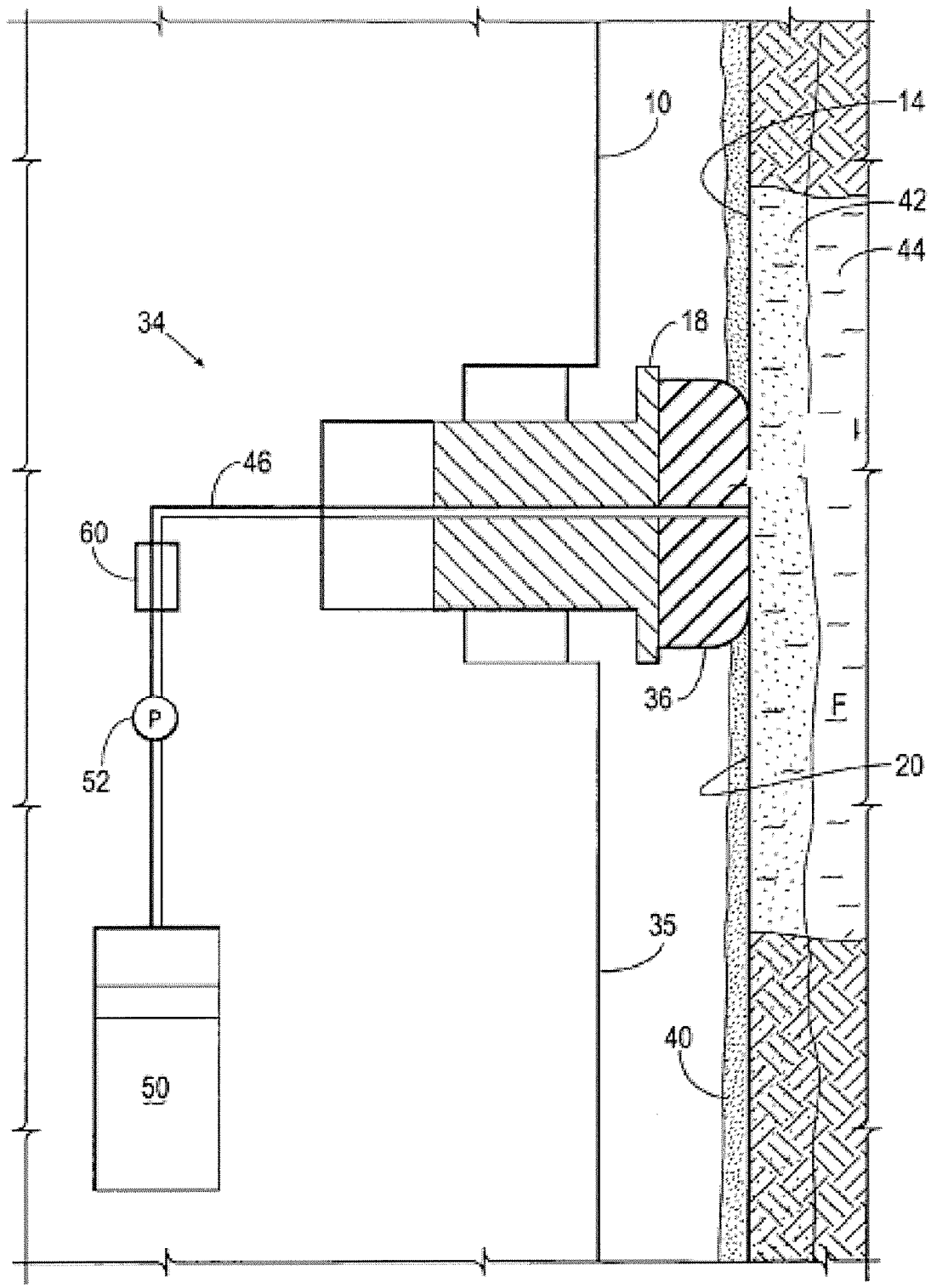
FIG. 3 is a schematic view of a fluid sampling system of the downhole tool of FIG. 1.

FIG. 3 is a schematic view of a portion of the downhole tool 10 of FIG. 1 depicting a fluid sampling system 34. The probe 18 is preferably extended from a housing 35 of the downhole tool 10 to engage the wellbore wall 20. The probe 18 is provided with a packer 36 for sealing against the wellbore wall 20. The packer 36 contacts the wellbore wall 20 and forms a seal between the fluid in the formation and the fluid in the wellbore with a mud cake 40 lining the wellbore 14. Portions of the mud seep into the wellbore wall 20 and create an invaded zone 42 about the wellbore 14. The invaded zone 42 contains mud and other wellbore fluids that contaminate the surrounding formations, including the formation F and a portion of the virgin fluid 44 contained therein. The seal between the fluid in the formation and the fluid in the mud may be provided by a dual packer type of module or any other packer and/or probe.

The probe 18 is preferably provided with an evaluation flow line 46. Examples of fluid communication devices, such as probes and dual packers, used for drawing fluid into a flow line are depicted in U.S. Pat. Nos. 4,860,581 and 4,936,139.

The evaluation flowline 46 extends into the downhole tool 10 and is used to pass fluid, such as virgin fluid 44 into the downhole tool 10 for testing and/or sampling. The evaluation flowline 46 extends to a sample chamber 50 for collecting samples of the virgin fluid 44. A pump 52 may be used to draw fluid through the flowline 46.

While FIG. 3 shows a sample configuration of a downhole tool used to draw fluid from a formation, it will be appreciated by one of skill in the art that a variety of configurations of probes, flowlines and downhole tools may be used and is not intended to limit the scope of the invention.

In accordance with the teachings of the present disclosure, a viscometer 60 is associated with an evaluation cavity within the downhole tool 10, such as the evaluation flowline 46 for measuring the viscosity of the fluid within the evaluation cavity. Example implementations of the viscometer 60 are shown in more detail in FIGS. 4, 5, 6, and 7. The viscometer 60 may be positioned at different locations along the evaluation flowline 46.

The downhole tool 30 may also be provided with the housing 35, probe 18 fluid flow system 34, packer 36, evaluation flowline 46, sample chamber 50, pump(s) 52 and viscometer(s) 60 in a similar manner as the downhole tool 10.

Figure 4:
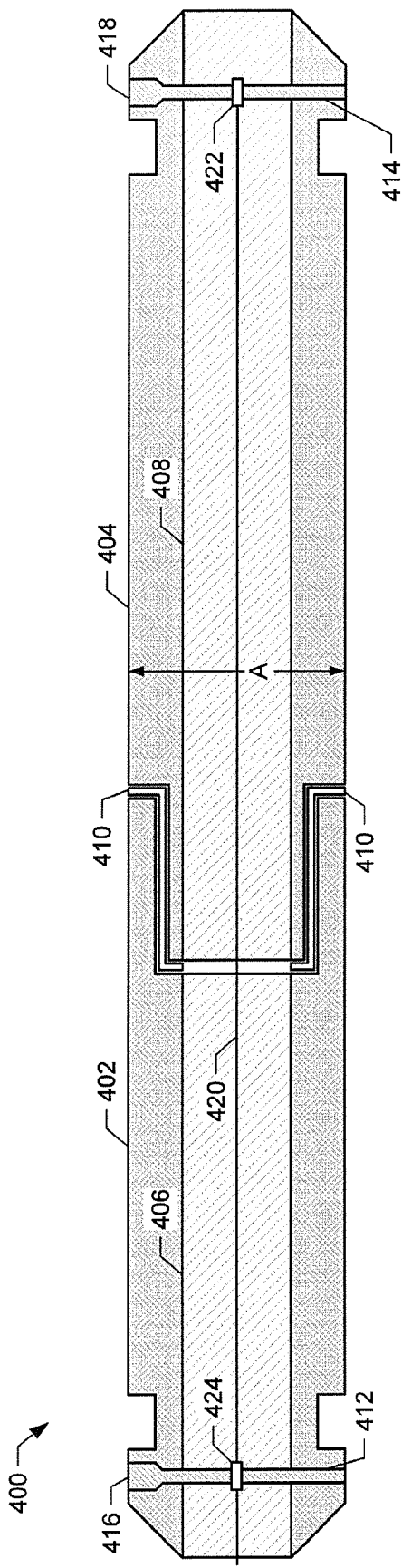
FIG. 4 is a schematic diagram of an example vibrating wire viscometer.

FIG. 4 is a schematic diagram of an example vibrating wire viscometer 400. The vibrating wire viscometer 400 may be used to implement the example viscometer 60 of FIG. 3 to measure the viscosity of a downhole fluid within a downhole tool. When subjected to increased temperature conditions in a downhole environment, the example vibrating wire viscometer 400 retains measurement accuracy by expanding uniformly. The vibrating wire described below maintains a substantially constant tension and, thus, vibrates at a predictable frequency in response to a given fluid viscosity.

The example vibrating wire viscometer 400 includes two electrically conductive tubes 402 and 404. The example tubes 402 and 404 are generally cylindrical in shape and have substantially the same outer diameter A. Additionally, the tubes 402 and 404 include respective flowlines 406 and 408. The example flowlines 406 and 408 are cylindrical and concentric with the longitudinal axes of the tubes 402 and 404. However, the flowlines 406 and 408 may also have any other shape and/or be located in any other manner within the tubes 402 and 404 that does not cause a substantial flow disturbance while measuring the viscosity of a downhole fluid sample.

The tube 404 may be partially inserted into the tube 402 to align the flowlines 406 and 408. While each of the tubes 402 and 404 is electrically conductive, the tubes 402 and 404 are electrically decoupled or insulated from each other by a non-conductive bonding agent 410 applied to the tubes 402 and 404. The non-conductive bonding agent 410 is applied to the tubes 402 and 404 such that when the tube 404 is inserted into the tube 402, the non-conductive bonding agent 410 lies between the tubes 402 and 404 at any locations that the tubes 402 and 404 might otherwise make mechanical and electrical contact. Additionally, the non-conductive bonding agent 410 permanently or substantially permanently mechanically couples the tubes 402 and 404.

The tubes 402 and 404 further include apertures or holes 412 and 414 into which respective pins 416 and 418 may be inserted. The holes 412 and 414 may be tapered to fit the pins 416 and 418 tightly when inserted. In other words, the pins 416 and 418 may be press fit into the holes 412 and 414. In the illustrated example, the tubes 402 and 404 are aligned such that the holes 412 and 414 (and, thus, the pins 416 and 418) are aligned (i.e., parallel). Orienting the pins 416 and 418 to be parallel to each other may help prevent twisting of a wire 420 fastened to and held in tension between the pins 416 and 418. Preventing twisting of the wire 420 may increase the accuracy of the viscometer 400.

To fasten the wire 420 to the pin 418, the wire 420 may be inserted into a crimp connector 422 in the pin 418. The crimp connector 422 is crushed or crimped around the wire 420 to fasten or fix the wire 420 to the pin 418. Such crimping or crushing of the connector 422 may be performed using, for example, a pliers or any other crushing or crimping tool. Similarly, to fasten the wire 420 to the pin 416, the wire may be inserted into a crimp connector 424 in the pin 416. To apply appropriate tension to the wire 420, a tensile force may be applied to the end of the wire 420 prior to and/or while crimping or crushing. The crimp connector 424 is then crushed or crimped around the wire 420 to fasten or fix the wire 420 to the pin 416. When the pin 420 has been fastened to both pins 416 and 418, the wire 420 has a tension that remains substantially constant. Other methods may also be used to place a tension on the wire 420 between the pins 416 and 418 within the flowlines 406 and 408.

Heat and/or pressure in a downhole environment may cause the tubes 402 and 404, the non-conductive bonding agent 410, the pins 416 and 418, and/or the wire 420 to expand or contract, which could cause the tension of the wire 420 to change. A change in the tension of the wire 420 may alter the vibration and/or resonance characteristics of the wire 420 and, thus, the accuracy of measurements made with the viscometer 420. To prevent the tension on the wire 420 from substantially changing, the materials chosen to implement the tubes 402 and 404, the non-conductive bonding agent 410, the pins 416 and 418, and the wire 420 may be chosen to have similar and/or substantially identical thermal expansion coefficients. In some examples, the tubes 402 and 404, the pins 416 and 418, and/or the wire 420 are implemented using tungsten, which has a linear thermal expansion coefficient of approximately 4.5 parts per million per degree Celsius (ppm/° C.). The non-conductive bonding agent 410 may then be implemented using, for example, a glass, ceramic, and/or non-conductive epoxy material having a substantially similar linear thermal expansion coefficient (e.g., 3 ppm/° C.-7 ppm/° C.). As a result, thermal expansion/contraction of the tubes 402 and 404, the non-conductive bonding agent 410, the pins 416 and 418, and the wire 420 may occur similarly and/or substantially equally, so that the wire 420 tension does not substantially change.

Figure 5A:
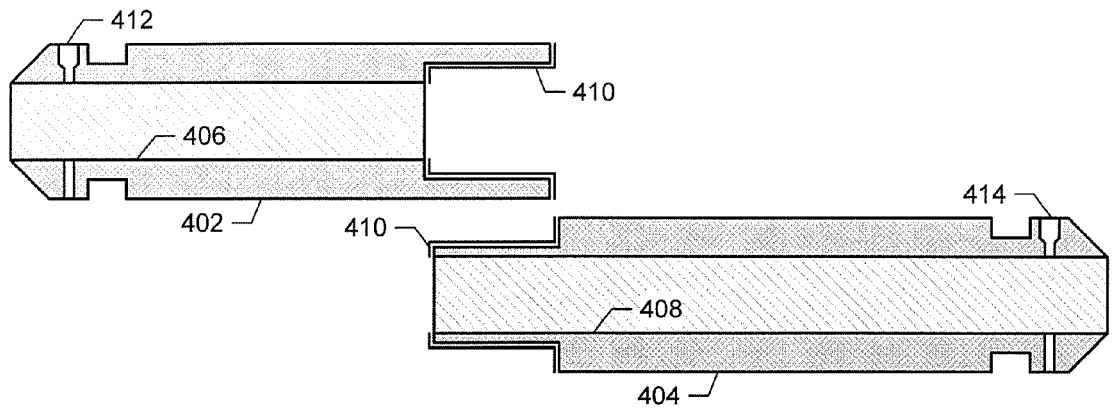
FIGS. 5A-5E illustrate operations of an example process to assemble the vibrating wire viscometer illustrated in FIG. 4.

FIGS. 5A-5E illustrate steps of an example process to assemble the example vibrating wire viscometer 400 illustrated in FIG. 4. FIG. 5A illustrates the conductive tubes 402 and 404 separated. Prior to inserting the tube 404 into the tube 402, the non-conductive bonding agent 410 is applied to the portions of the tubes 402 and 404 that would otherwise make direct mechanical and electrical contact when assembled.

Figure 5B:
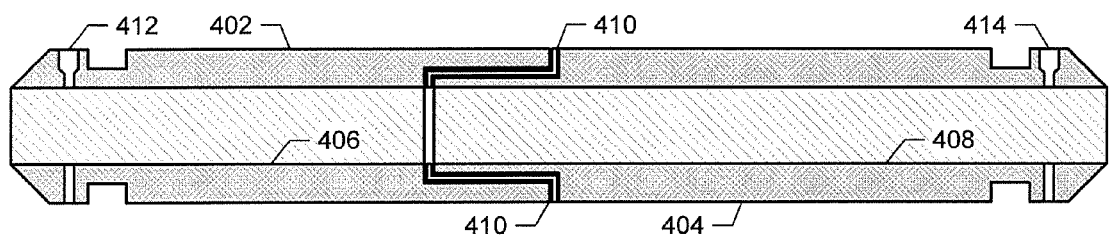

After applying the non-conductive bonding agent 410 to the tubes 402 and 404, the tube 404 is inserted into the tube 402 as illustrated in FIG. 5B. The non-conductive bonding agent 410 permanently or substantially permanently mechanically couples the tubes 402 and 404 to each other while electrically decoupling or insulating the tubes 402 and 404 from each other. When the tubes 402 and 404 are mechanically coupled, the holes 412 and 414 may be aligned such that the pins, when inserted, are parallel.

Figure 5C:
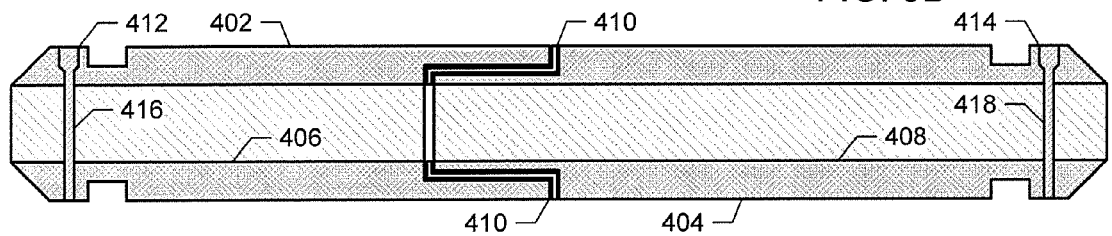

The pins 416 and 418 are then inserted into the holes 412 and 414 as shown in FIG. 5C. The pins 416 and 418 are aligned in a parallel manner due to the orientation of the holes 412 and 414. Additionally, the pins 416 and 418 are tightly fit (e.g., press fit) into the holes 412 and 414 to retain the pins 416 and 418.

Figure 5D:
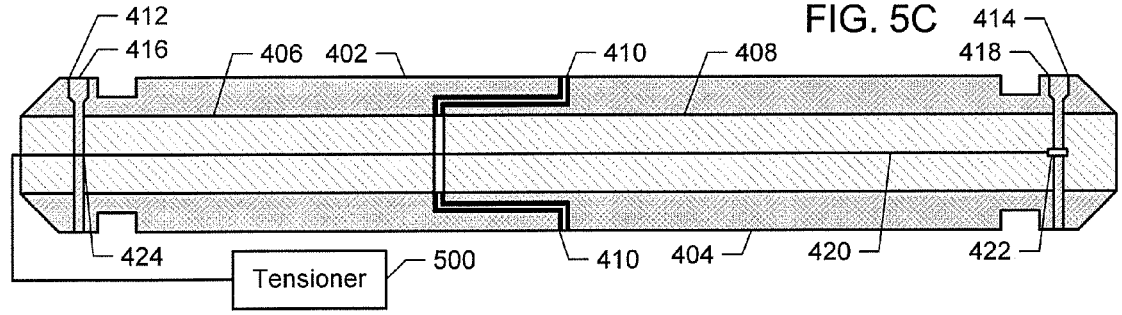

One end of the wire 420 is then inserted into the crimp connector 422 on the pin 418 and the crimp connector 422 is crimped or crushed to fasten the wire 420 to the pin 418. As illustrated in FIG. 5D, the other end of the wire 420 is passed through the flowlines 406 and 408, through the crimp connector 424, and to a tensioner 500. The crimp connector 424 is not yet crimped or crushed to fasten the wire 420. Instead, the tensioner 500 applies a force to the wire 420 such that the wire 420 between the pins 416 and 418 has a desired tension. The tensioner 500 may further ensure that the wire 420 is not twisted because twisting of the wire 420 may affect the resonance frequency, damping, and/or the measurement accuracy of the vibrating wire viscometer 400.

Figure 5E:
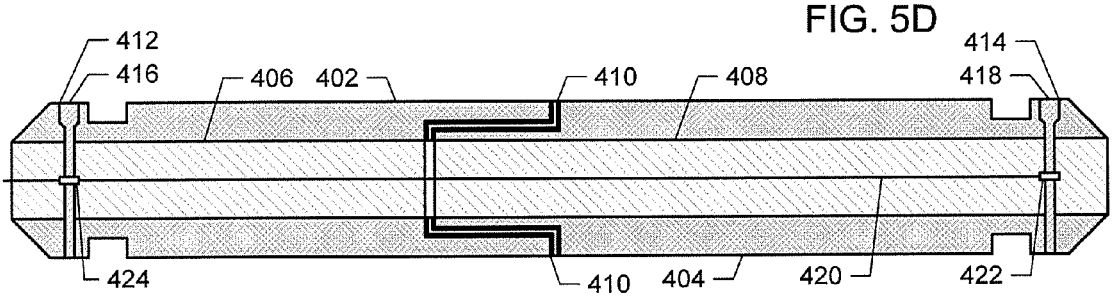

When the wire 420 is untwisted and at the desired tension, the crimp connector 424 may be crimped or crushed as illustrated in FIG. 5E to fasten the wire 420 to the pin 416. As a result, the wire 420 is fastened between the pins 416 and 418 at the desired tension to produce a desired resonance frequency response.

Figure 6:
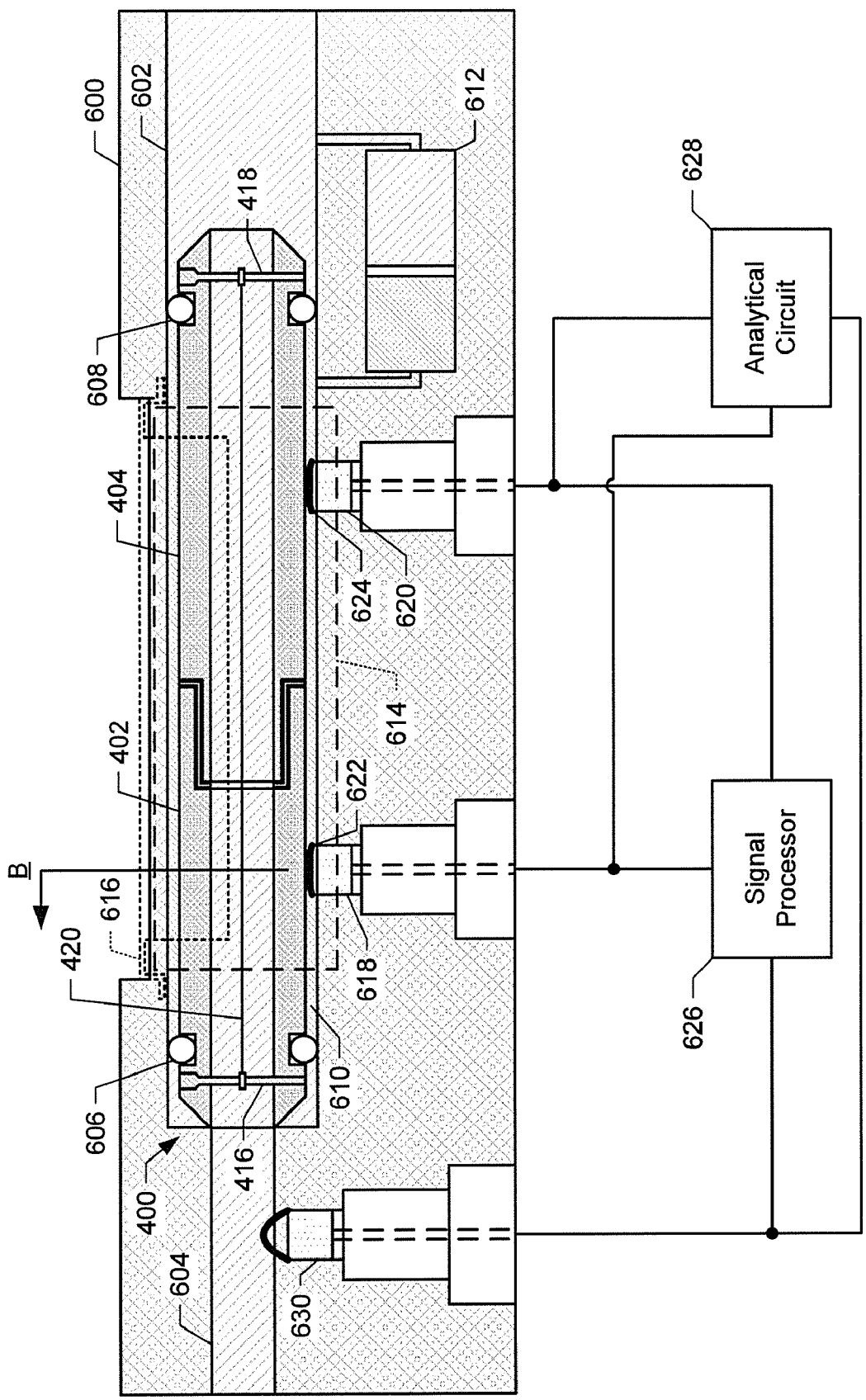
FIG. 6 is a schematic diagram of the example vibrating wire viscometer of FIG. 4 in a high pressure housing.

FIG. 6 is a schematic diagram of the example vibrating wire viscometer 400 of FIG. 4 in a housing 600. The housing 600 may be used to mount or support the vibrating wire viscometer 400 in, for example, the downhole tool 10 described in connection with FIGS. 1 and 3.

The example vibrating wire viscometer 400 is inserted into the housing 600 via a flowline 602. Downhole fluid may enter and/or exit the flowlines 406 and 408 of the vibrating wire viscometer 400 via, for example, the flowline 602 and a second, smaller flowline 604. The downhole fluid may flow through the flowlines 602 and 604 within a large range of temperatures and pressures. To provide support within the flowline 602, the vibrating wire viscometer 400 may be provided with seals 606 and 608. The seals 606 and 608 prevent electrically conductive downhole fluids from surrounding the example tubes 402 and 404 at the point where the tubes 402 and 404 meet. Instead, the example vibrating wire viscometer 400 is surrounded by a non-conductive fluid 610, such as silicone oil, between the two seals 606 and 608. The example seals 606 and 608 are sufficiently stiff to provide support and sealing, but sufficiently soft to allow small deformations of the tubes 402 and 404 caused by heat and pressure.

To balance the pressure between fluid in the flowline 602 and the non-conductive fluid 610, the example housing 600 includes a pressure compensator 612. The pressure compensator 612 is fluidly coupled to the flowline 602 and the non-conductive fluid 610 to balance the pressure exerted on the vibrating wire viscometer 400. As the pressure in the flowline 602 increases, the pressure compensator 612 transfers the pressure to the non-conductive fluid 610. As a result, the tubes 402 and 404 are pressure balanced and are not prevented from expanding or contracting by differences in fluid pressure.

The example housing 600 further includes one or more magnets 614 to create a magnetic field. Vibration is induced in the wire 420 by the magnetic field when, for example, an alternating current is applied to the wire 420 at or near the resonance frequency of the wire 420. The magnetic field vibrates the wire 420 when a signal is applied to the wire 420 at the desired resonance frequency. The magnet(s) 614 may be inserted into the housing 600 via a cover 616. It is known that even high-quality wire may not be perfectly cylindrical, and instead may have an elliptical cross-section. The tubes 402 and 404 may be oriented within the flowline 602 so that the major axis of the elliptical cross-section of the wire 420 is aligned with the magnetic field provided by the magnet(s) 614.

The housing 600 is further provided with electrodes 618 and 620, which include spring contacts 622 and 624 to apply slight mechanical pressure on the electrodes 618 and 620 to make electrical contact with respective ones of the tubes 402 and 404. The electrodes 618 and 620 (i.e., spring contacts 622 and 624) are electrically coupled to a signal processor 626 and an analytical circuit 628. The signal processor 626 generates a sinusoidal waveform at a desired frequency. The alternating current signal generated by the signal processor 626 is transmitted to the wire 420 via a signal path including the electrodes 618 and 620, the spring contacts 622 and 624, the tubes 402 and 404, the pins 416 and 418, and the wire 420.

As the signal processor 626 generates the sinusoidal waveform while the wire 420 is within the magnetic field, the wire 420 resonates and vibrates at a known resonant frequency. Based on the viscosity of the downhole fluid, either the vibration amplitude decreases by a deterministic amount or additional power is required to maintain the vibration amplitude of the wire 420. Under either scenario, an electromotive force voltage is generated by the vibration of the wire 420 within the magnetic field generated by the magnets 614. The analytical 628 circuit monitors the electromotive force voltage, a damping and/or a quality factor to determine the viscosity of the downhole fluid. The operational determination of the viscosity of a downhole fluid is described in more detail in U.S. Pat. No. 7,222,671.

The example housing 600 further includes a temperature sensor 630. The temperature sensor 630 determines the temperature of the downhole fluid in the flowline 604 when the viscosity measurement is performed. The temperature sensor 630 is electrically coupled to the signal processor 626 and/or the analytical circuit 628. Based on the sensed temperature, the example signal processor 626 may adjust the resonant frequency and/or the analytical circuit 628 may extrapolate the determined viscosity of the downhole fluid at the detected temperature to viscosities of the downhole fluid at other temperatures using known temperature-viscosity relationships.

Figure 7:
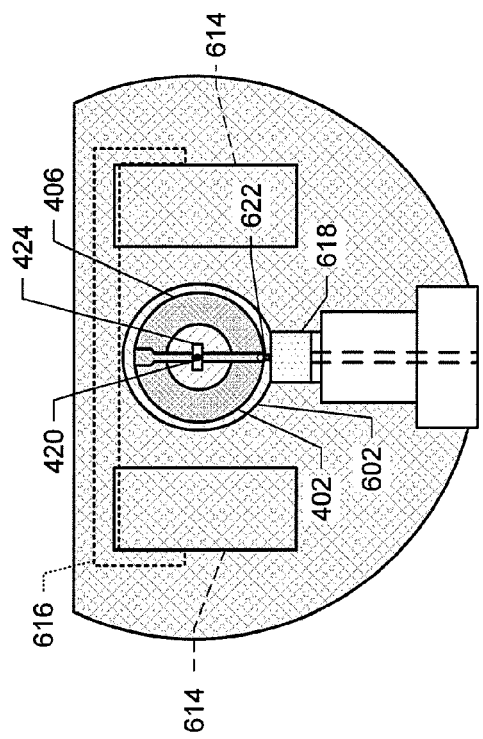
FIG. 7 is another view of the example vibrating wire viscometer and high pressure housing of FIG. 6.

FIG. 7 is another view of the example vibrating wire viscometer 400 and housing 600 of FIG. 6. The view of FIG. 7 is taken from the viewpoint B illustrated in FIG. 6. The example view illustrated in FIG. 7 shows the positioning of the magnets 614 on both sides of the wire 420. The crimp 424 and the wire 420 are shown slightly larger in FIG. 7 than in FIGS. 4-6 for clarity purposes. The example temperature sensor 630 is not shown in FIG. 7 to more clearly show the example electrode 618 and the example spring contact 622. The electrode 620 and the spring contact 624 are obscured in FIG. 7 by the electrode 618 and the spring contact 622, respectively. However, the electrode 620 and the spring contact 624 may be similar, identical to, or different than the electrode 618 and the spring contact 622.

Although example methods, apparatus and articles of manufacture have been described herein, the scope of coverage of this patent is not limited thereto. On the contrary, this patent covers every apparatus, method and article of manufacture fairly falling within the scope of the appended claims either literally or under the doctrine of equivalents.

What is claimed is:

1. A vibrating wire viscometer, comprising:
   first and second electrically conductive tubes, wherein the first electrically conductive tube is at least partially inserted into the second electrically conductive tube, and wherein the first and second electrically conductive tubes are coupled via an electrically non-conductive bonding agent;
   the first and second tubes are disposed in a housing to receive the downhole fluid via a housing flowline, wherein the tubes comprise a plurality of supporting seals coupled circumferentially to support the first and second tubes within the housing flowline, and wherein the first and second tubes are immersed in an electrically insulating fluid disposed between the supporting seals, the first and second tubes, and the housing;
   first and second electrically conductive pins inserted into respective ones of the first and second tubes; and
   an electrically conductive wire fastened to the first and second pins to vibrate in a downhole fluid to determine a viscosity of the downhole fluid.

2. The vibrating wire viscometer as defined in claim 1, wherein the first and second tubes, the bonding agent, the first and second pins, and the wire comprise substantially equal thermal expansion coefficients.

3. The vibrating wire viscometer as defined in claim 1, wherein the wire has a predetermined tension between the first and second pins.

4. The vibrating wire viscometer as defined in claim 1, wherein the wire is fastened to the first pin by crimping.

5. The vibrating wire viscometer as defined in claim 4, wherein the wire is fastened to the second pin by crimping.

6. The vibrating wire viscometer as defined in claim 1, further comprising first and second electrical contacts electrically coupled to respective ones of the first and second tubes to apply a signal to the wire.

7. The vibrating wire viscometer as defined in claim 6, further comprising a magnet adjacent to the wire.

8. The vibrating wire viscometer as defined in claim 1, further comprising an analyzer to determine the viscosity of the downhole fluid by measuring a reverse voltage of the wire.

9. The vibrating wire viscometer as defined in claim 1, wherein the wire and the first and second tubes comprise tungsten.

10. The vibrating wire viscometer as defined in claim 1, wherein the first and second tubes are disposed in a housing to receive the downhole fluid via a housing flowline.

11. The vibrating wire viscometer as defined in claim 10, further comprising a first spring to make electrical contact with the first tube in the housing and a second spring to make electrical contact with the second tube in the housing.

12. The vibrating wire viscometer as defined in claim 10, further comprising a plurality of supporting seals coupled circumferentially to support the first and second tubes within the housing flowline.

13. The vibrating wire viscometer as defined in claim 12, wherein the first and second tubes are immersed in an electrically insulating fluid disposed between the supporting seals, the first and second tubes, and the housing.

14. The vibrating wire viscometer as defined in claim 13, further comprising a pressure compensator to equalize a fluid pressure between the electrically insulating fluid and the downhole fluid in the housing flowline.

15. The vibrating wire viscometer as defined in claim 1, wherein the first and second pins are parallel.

16. A vibrating wire viscometer, comprising:
   first and second electrically conductive tubes disposed in a housing, wherein the first tube is at least partially inserted into the second tube, and wherein the first and second tubes are coupled via an electrically insulating bonding agent;
   the first and second tubes comprise a plurality of supporting seals coupled circumferentially to support the first and second tubes within the housing flowline, wherein the first and second tubes are immersed in an electrically insulating fluid disposed between the supporting seals, the first and second tubes, and the housing;
   first and second electrically conductive pins inserted in parallel into respective ones of the first and second tubes;
   an electrically conductive wire held in tension between the first and second pins to vibrate in a downhole fluid in the first and second tubes; a magnet to generate a magnetic field adjacent the wire;
   a signal processor to generate an electrical signal to cause the wire to vibrate at a resonance frequency in the magnetic field; and
   an analyzer to measure a reverse voltage of the wire to determine a viscosity of the downhole fluid.

17. The vibrating wire viscometer as defined in claim 16, further comprising a plurality of supporting seals coupled circumferentially to support the first and second tubes within the housing.

18. The vibrating wire viscometer as defined in claim 17, wherein the first and second tubes are immersed in an electrically insulating fluid disposed between the supporting seals, the first and second tubes, and the housing.

19. The vibrating wire viscometer as defined in claim 18, further comprising a pressure compensator to equalize a fluid pressure between the electrically insulating fluid and the downhole fluid in the housing flowline.

20. A vibrating wire viscometer, comprising:
   first and second electrically conductive tubes, wherein the first tube is at least partially inserted into the second tube, and wherein the first and second tubes are coupled via an electrically insulating bonding agent;
   first and second electrically conductive pins inserted into respective ones of the first and second tubes;
   an electrically conductive wire held in tension between the first and second pins to vibrate in a downhole fluid in the first and second tubes; and a housing comprising:
   a flowline, wherein the first and second tubes are disposed in the flowline;
   the first and second tubes comprise a plurality of supporting seals coupled circumferentially to support the first and second tubes within the housing flowline, wherein the first and second tubes are immersed in an electrically insulating fluid disposed between the supporting seals, the first and second tubes, and the housing;
   a magnet disposed in the housing to generate a magnetic field adjacent the wire;
   a signal processor to generate an electrical signal to vibrate the wire in the magnetic field at a resonance frequency; and
an analyzer to measure a reverse voltage on the wire to determine a viscosity of the downhole fluid.

* * * * *